(12) United States Patent
Sundbom Nilsson et al.

(10) Patent No.: US 9,492,407 B2
(45) Date of Patent: Nov. 15, 2016

(54) TOPICAL FORMULATION FOR TREATMENT OF HYPERKERATOTIC SKIN

(75) Inventors: Johan Sundbom Nilsson, Stocksund (SE); Marie Lodén, Solna (SE)

(73) Assignee: AUXILIUM CURA INNOVATIO, Dublin (IE)

( * ) Notice: Subject to any disclaimer, the term of this patent is extended or adjusted under 35 U.S.C. 154(b) by 85 days.

(21) Appl. No.: 14/116,831

(22) PCT Filed: May 14, 2012

(86) PCT No.: PCT/SE2012/050514
§ 371 (c)(1),
(2), (4) Date: Nov. 11, 2013

(87) PCT Pub. No.: WO2012/154122
PCT Pub. Date: Nov. 15, 2012

(65) Prior Publication Data
US 2014/0073613 A1    Mar. 13, 2014

Related U.S. Application Data

(60) Provisional application No. 61/485,287, filed on May 12, 2011.

(30) Foreign Application Priority Data

May 12, 2011    (EP) .................................. 11165916

(51) Int. Cl.
| | | |
|---|---|---|
| *A61K 9/107* | (2006.01) | |
| *A61K 31/164* | (2006.01) | |
| *A61K 31/17* | (2006.01) | |
| *A61K 31/19* | (2006.01) | |
| *A61K 31/16* | (2006.01) | |
| *A61K 45/06* | (2006.01) | |
| *A61K 9/00* | (2006.01) | |
| *A61K 31/047* | (2006.01) | |

(52) U.S. Cl.
CPC ............. *A61K 31/16* (2013.01); *A61K 9/0014* (2013.01); *A61K 9/107* (2013.01); *A61K 31/047* (2013.01); *A61K 31/164* (2013.01); *A61K 31/17* (2013.01); *A61K 31/19* (2013.01); *A61K 45/06* (2013.01)

(58) Field of Classification Search
CPC .... A61K 9/107; A61K 31/164; A61K 31/17; A61K 31/19; A61K 31/16; A61K 45/06
See application file for complete search history.

(56) References Cited

U.S. PATENT DOCUMENTS

| 5,776,920 A | 7/1998 | Quarles et al. | |
|---|---|---|---|
| 2010/0068161 A1* | 3/2010 | Todary Michael | 424/59 |

FOREIGN PATENT DOCUMENTS

| WO | 8704617 A1 | 8/1987 |
|---|---|---|
| WO | 2005016329 A1 | 2/2005 |

OTHER PUBLICATIONS

Hyerkeratosis, 2016, https://pharmavel.com/en/products/afroloytra-amp-swma/kremes-knhsmos-erethismeno-derma-IRRITATED%20SKIN-%20CREAM/5197-healderm-lacurex-ointment-150ml.*
"Final Report on the Safety Assessment of Panthenol and Pantothenic Acid" International Journal of Toxicology, vol. 6, No. 1 (1987), pp. 139-162.
Ademola et al., "Clinical Evaluation of 40% Urea and 12% Ammonium Lactate in the Treatment of Xerosis", American Journal of Dermatology. 3:3, (2002), pp. 217-222.
Andersen "Final report of the Safety Assessment of Urea" International Journal of Toxicology; vol. 24m No. SUPPL. 3, (2005), pp. 1-56.
Ashton et al., "Urea as a Topical Agent" Therapeutics XIII, 87 (1971), pp. 194-196.
Dahl et al., "12% Lactate Lotion for the Treatment of Xerosis" Arch Dermatol, vol. 119, Jan. 1983, pp. 27-30.
Dexpanthenol, CAS—81-13-0 Retrieved from Martindale, The Complete Drug Regerence, 34th Edition, Published Jan. 2005.
Doering et al., German Patent Application No. 10133195.9 (A1), Date of Publication: Jan. 16, 2003, With English Abstract.
European Search Report for European Application No. 12167943; Date of Mailing: Jun. 5, 2012; 6 Pages.
Fritsch et al., "Ultrastructural Changes in Onychomycosis During the Treatment with Bifonazole/Urea Ointment" Dermatology, 185, (1992), pp. 32-36.
Garg et al., "Long Term Topical Application of Lactic Acid/Lactate Lotion as a Preventitive Treatment for Acne Vulgaris", Indian J. Dermatol Venereol Leprol, 67, (2002), pp. 137-139.
Green et al., "A Comparison Study of 7.5% Lactic Acid Cream and 12% Lactic Acid Lotion in Psoriatic Patients with Xerosis Cuts" Cosmetic Dermatology, vol. 7, No. 5, May 1994, pp. 44-15.
Green et al., "Clinical and Cosmeceutical Uses of Hydroxyacids" Clinics in Dermatology, vol. 27, No. 5, (Sep. 1, 2009), pp. 495-501.
Hellgren et al., "On the Effect of Urea on Human Epidermis" Dermatologica, 149, (1974), pp. 289-293.

(Continued)

*Primary Examiner* — Sun Jae Yoo
(74) *Attorney, Agent, or Firm* — Cantor Colburn LLP

(57) ABSTRACT

The present invention relates in general to topical compositions having improved antimicrobial effect useful for the treatment of hyperkeratotic skin conditions. More specifically, the present invention relates to topical compositions comprising a combination of one or more alpha-hydroxy acids, urea, glycerol, and panthenol, as well as the use of such compositions for the treatment of hyperkeratotic skin conditions, in particular on the feet, and also on other body areas where thick skin is noted and where infections should be avoided.

14 Claims, No Drawings

(56) References Cited

OTHER PUBLICATIONS

International Preliminary Report on Patentability for International Patent Application No. PCT/SE2012/050514; International Filing Date: May 14, 2012; Date of Completion: Jun. 4, 2013; 9 Pages.
International Search Report of the International Searching Authority for International Patent Application No. PCT/SE2012/050514; International Filing Date: May 14, 2012; Date of Mailing: Nov. 13, 2012, 5 Pages.
Jacobi, "Moisture Regulation in the Skin" Drug and Cosmetic Industry; 84, 6, Jun. 1959, 5 Pages.
Kim et al., "Effect of Lactic Acid on Listeria Monocytogenes and Edwardsiella Tarda Attached to Catfish Skin" Food Microbiology, 18, (2001), pp. 589-596.
Kuntz et al., "Hydration of Macromolecules. II. Effects of urea on Protein Hydration" Archives of Biochemistry and Biophysics, 142 (1971), pp. 660-664.
Lacurex Ointment Package Insert, as printed from http://www.healderm.com/lacurexplus.pdf on Mar. 21, 2014.
Loden et al., "Clinical Evidence for the Use of Urea" Dry Skin and Moisturizers: Chemistry and Function, 19, (2005), pp. 211-225.
Loden et al., "Prevention or Promotion of Dryness and Eczema by Moisturizers?" Expert Rev. Dermatol. (3(6); (2008); pp. 667-676.
Middleton "Development of a Skin Cream Designed to Reduce Dry and Flaky Skin" J. Society of Cosmetic Chemists of Great Britain, 25 (1974), pp. 519-537.
Nishijima, "Recent Treatment for Acne Vulgaris" Skin Research, vol. 3(6), (2004), pp. 622-627, Abstract Only. XP-002659031.
Oji et al., "Ichthyosis, Clinical Manifestations and Pratical Treatment Options" American Journal Clin. Dermatology, 10 (6), (2009) pp. 351-364.
Prall et al., "The Effectiveness of Cosmetic Products in Alleviating a Range of Skin Dryness Conditions as Determined by Clinical and Instrumental Techniques" International Journal of Cosmetic Science, 8, (1986), pp. 159-174.

Proksch et al., "Dexpanthenol Enhances Skin Barrier Repair and Reduces Inflammation after Sodium Lauryl Sulphate-Induced Irritation" Journal of Dermatological Treatment, 13, (2002), pp. 173-178.
Regulation (EC) No. 1223/2009 of the European Parliament and of the Council of Nov. 30, 2009 on Cosmetic Products; Official Journal of the European Union; Dec. 22, 2009, pp. L342/59-L342/209.
Rogers et al., "Comparative Efficacy of 12% Ammonium Lactate Lotion and 5% Lactic Acid Lotiion in the Treatment of Moderate to Severe Xerosis" Journal of American Academy of Dermatology, vol. 21, No. 4, Part 1, Oct. 1989, pp. 714-716.
Schmid-Grendelmeier et al., "Contact Allergy to Dexpantheonl"; Dermatosen / Occup. Environ. 43; (1995); pp. 175-178.
Swanbeck, "A New Treatment of Ichyhyosis and Other Hyperkeratotic Conditions" Acta Derm-Venereol. 18, (1968), pp. 123-127.
Traupe et al., "Treatment of Ichthyosis—There is Always Somethign you Can Do! In Memoriam: Wolfang Kuster" Journal of the American Academy of Dermatology, vol. 57, No. 3, Aug. 15, 2007, pp. 542-547.
Vilaplana et al., "Clinical and Non-invasive Evaluation of 12% Ammonium Lactate Emulsion for the Treatment of Dry Skin in Atopic and Non-atopic Subjects" Acta Derm Venereol, 72, (1992), pp. 28-33.
Wehr et al., "A Controlled Comparative Efficacy Study of 5% Ammonium Lactate Lotion Versus and Emollient Control Lotion in the Treatment of Moderate Xerosis" Journal of the American Academy of Dermatology, vol. 25, No. 5, Part 1, Nov. 1991, pp. 84.
Wehr et al., "A Controlled Two-Center Study of Lactate 12 Percent Lotion and a Petrolatum-Based Creme in Patients with Xerosis" Therapeutics for the Clinician, New Reports on treatment of Modalities of Possible Interest to Patient-Caring Physicians, PD-64.
Written Opinion of the International Searching Authority for International Patent Application No. PCT/SE2012/050514; International Filing Date: Mar. 14, 2012, 9 Pages.

* cited by examiner

TOPICAL FORMULATION FOR TREATMENT OF HYPERKERATOTIC SKIN

CROSS-REFERENCE TO RELATED APPLICATIONS

This Application is a U.S. National Stage Application of PCT/SE2012/050514 filed May 14, 2012, which claims priority from European Patent Application No. 11165916.5, filed May 12, 2011, and U.S. Provisional Application No. 61/485,287, filed May 12, 2011, both of which are incorporated by reference in their entirety.

FIELD OF THE INVENTION

The present invention relates in general to topical compositions useful for the treatment of hyperkeratotic skin conditions. More specifically, the present invention relates to topical compositions comprising a combination of: one or more alpha-hydroxy acids comprising lactic acid and/or glycolic acid; urea; glycerol; and panthenol, as well as the use of such compositions for the treatment of hyperkeratotic skin conditions, in particular on the feet, and also on other body areas where thick skin is noted and where infections should be avoided.

BACKGROUND OF THE INVENTION

Stratum corneum is a tough and almost impermeable outer layer of the body, consisting of stacked layers of corneocytes. The corneocytes are the end product of the keratinocytes which are continuously produced in the basal layer of the epidermis. The loss of single corneocytes at the skin surface (desquamation) takes place in a controlled manner in healthy skin. At equilibrium the rate of epidermal cell production corresponds to the loss of desquamative cells and a smooth, luminous skin is observed. However, this desquamation, also called exfoliation, is easily disturbed resulting in a build-up of corneocytes on the surface, observed as a thickening of the surface (hyperkeratosis) and cracks with various depths. When corneocytes fail to separate from one another also scaling can also be observed, i.e. shedding of clumps of stratum corneum cells.

Enzymes involved in the desquamation process are dependent upon water for activity. The presence of water also influences the physical properties of the stratum corneum. After a long bath when the stratum corneum is superhydrated it is easy to rub off the surface layer of the skin, signifying the importance of water for the activity of the enzymes. The opposite is observed during dry condition when the desquamation is retarded due to increased cohesion of cells.

Hyperkeratotic and scaling disorders include ichthyosis, psoriasis, cradle cap, dandruff, keratosis, callus, acne and xerosis. Xerosis is defined as dehydration of skin characterized by redness, dry scaling, and fine crackling that may resemble the crackling of porcelain.

Xerosis and cracking of the skin are common on the feet and get worse with wearing open-back shoes, increased weight, or increased friction from the back of shoes. Dry cracking skin of the feet can also be a subtle sign of more significant problems, such as diabetes or loss of nerve function (autonomic neuropathy). In the skin of diabetic feet the blood circulation is also deteriorated.

Treatment recommendation for xerotic feet with cracking skin is to keep skin in a good condition with creams/ointments to help reduce the cracking. Cracking of the skin can lead to open sores if the skin is not cured and healed properly. Skin infections promoted by the growth of microorganisms can develop into sores. If an open sore is noted, an appointment with a physician is recommended for evaluation and treatment. Open sores can be disastrous to people with diabetes and may in worst case lead to amputation.

On the market a number of related topical formulations are available. For example, one product, an ointment, called LacUrex (Healderm Hellas S. A.) contains 10% urea, 12% of ammonium lactate, and, i.a., also minor amounts of panthenol and glycerin.

Accordingly, it is an object of the present invention to provide a composition for exfoliating hyperkeratotic skin and normalization of the skin. For the purpose of proper healing, and enhanced normalization, it would be desirable to provide such composition having improved antimicrobial properties.

SUMMARY OF THE INVENTION

The present inventors have found that a combination of at least 15% by weight of one or more alpha-hydroxy acids comprising lactic acid and/or glycolic acid; at least 15% by weight of urea; at least 5% by weight of glycerol; and, at least 5% by weight of panthenol will provide a keratolytic composition having markedly improved antimicrobial properties, as compared to currently available commercial products designed for hyperkeratotic treatment, especially for feet.

Accordingly, in one aspect the invention relates to a topical formulation containing the inventive combination of at least 15% by weight of one or more alpha-hydroxy acids comprising lactic acid and/or glycolic acid, at least 15% by weight of urea, at least 5% by weight of glycerol, and, at least 5% by weight of panthenol.

Due to the antimicrobial properties of the above inventive combination of active agents, the inventive composition does not require the presence of conventional preservatives and antimicrobial agents, such as e.g. phenoxyethanol, parabenes, triclosan, benzalkonium chloride, chlorhexidine, phenoxyisoproanol, diazolidinyl urea, climbazol, DMDM hydantoin, sorbic acid, dehydroacetic acid and other preservatives found in cosmetics[1].

Also, by virtue of the improved antimicrobial properties, healing and normalization of the skin will be favoured, as skin infections thereby will be avoided, or ameliorated.

The present invention is primarily directed to treatment of hyperkeratotic skin conditions on the feet.

In a preferred embodiment, the present invention relates to a composition for treatment of dry sensitive feet in people with diabetes, which composition also increases skin blood circulation.

Dry hyperkeratotic skin, such as in eczema of the hands, atopic eczema, ichthyosis and psoriasis are also targeted diseases according to the invention. In addition, patients with acne are also believed to benefit from the treatment with the inventive composition, especially when salicylic acid is included in the inventive formulation.

All percentages herein are given by weight unless otherwise indicated.

DETAILED DESCRIPTION OF THE INVENTION

The majority of products available for treatment of xerosis and cracked heals are conventional moisturizers (cosmetics) with varying degree of efficacy on the dryness and potential drawbacks regarding their possibility to reduce the risks for infection and normalize the skin. Furthermore, these products do not promote the healing of the skin and do not contribute to the normalization of the blood flow in the area.

The present invention is directed to a topical preparation which uses a three-pronged approach where the combination of ingredients (a) targets the hyperkeratosis, (2) then the potential overgrowth of microorganisms on the skin surface, and, finally, (3) promotes normalization of the skin barrier to prevent further problem.

Treatment and prevention of hyperkeratosis involve increase in skin hydration, in addition to facilitate desquamation by the inclusion of substances known for such properties. The topical preparation of the present invention contains an optimal mixture of known keratolytic substances and ingredients known for their hydrating properties. Keratolytic substances have been used for long in the treatment of hyperkeratotic disorders. The term keratolytic indicates keratolysis, although the substances do not necessarily induce lysis of keratin but instead facilitate separation of the cells from one another. Some keratolytic substances, such as alpha-hydroxy acids (AHAs), appear to reduce the cohesion between the corneocytes and interfere with the bonding between the cells, which causes an increased cell turnover, especially at a pH around 3. Distinct changes in the epidermis are observed, which might mediate a prompt influence on the keratinization process. There is an abrupt loss of the entire abnormal stratum corneum (SC), probably due to a diminished cellular cohesion between the corneocytes at the lowermost, newly forming levels of the SC, at its junction with the stratum granulosum. AHAs, especially glycolic and lactic acid, are therefore beneficial for topical treatment of ichthyosis. In the art, a reduced number of stratum corneum layers has also been found in ichthyotic patients after treatment with 10% urea in combination with 5% lactic acid. Furthermore, in another study, a soft and pliable skin was obtained in seven patients with severe ichthyosis after treatment with a 10% urea formulation.

In the art, glycerin has been suggested to ameliorate dry flaky skin by facilitating the digestion of the corneodesmosomes in subjects with dry skin. Other agents may open up and unfold keratin (e.g. urea). In the present invention all three types are used at high concentrations, where the concentration of AHA is at least 15%, the concentration of glycerin is at least 5%, and the concentration of urea is at least 15%.

Salicylic acid may also be included at low concentrations, such as e.g. 0.1-4% to promote the keratolysis and further strengthen the antimicrobial properties of the formulation.

The invention also uses panthenol in an amount of at least 5%. Panthenol is an alcohol, which is converted in tissues to D-pantothenic acid (Vitamin B5), a component of coenzyme A in the human body.

In a preferred embodiment, the inventive composition may also include vitamin A (retinol), or derivates thereof, such as retinyl palmitate, retinoic acid, retinyl retinoate to facilitate the normalization of skin barrier and skin blood flow. Vitamin A is a fat-soluble vitamin essential for proper epithelial function, and its inclusion promotes normalization of the skin. When present, retinol or a derivative thereof, is preferably included in an amount of 0.01-2% by weight of the composition.

The inventive formulation may also contain blood flow stimulating agents such as nicotine amide (also known as niacinamide), esters of nicotinates (e.g. the methyl, ethyl, isopropyl, butyl, and benzyl esters) and L-arginin to restore the barrier and facilitate normalization of the skin.

The pH of the formulation will be kept low (typically at a pH of about 4) to facilitate the absorption of the AHAs and increase the efficacy of the product.

A low amount of an ordinary preservative, such as those mentioned in reference No. 1, may also be used in the formulation (e.g. 1% phenoxyethanol), along with a fatty alcohol, especially a mono- or di-hydric fatty alcohol (e.g. 1% caprylyl glycol), preferably a C8 to C12 mono- or di-hydric fatty alcohol, as an additional humectant with antimicrobial properties. The combination of such preservative with the fatty alcohol is believed to be synergistic in terms of antimicrobial effect.

Cetyl alcohol, cetearyl alcohol and behenyl alcohol are examples of fatty alcohols conventionally used as thickeners. Of these fatty alcohols behenyl alcohol is preferred as thickening agent in the inventive formulation. Cetyl alcohol is also known to be a skin sensitizing agent, whereas no such reports are available for behenyl alcohol. Behenyl alcohol is also reported to be effective against virus (herpes simplex). Thus, behenyl alcohol may reduce the likelihood for virus infections in the damaged skin, and is preferred for inclusion in the inventive composition also for this reason.

Menthol could also be included in the inventive composition, as it is believed to enhance the uptake of the active ingredients by bacteria, and thereby further improve the antimicrobial effect.

Unexpectedly, the inventive combination of substances (humectants, keratolytics and normalization substances) at the high overall concentration (at least 40%) makes the formulation extremely efficacious regarding the important antimicrobial efficacy. As can be seen from the testing results in Table 3, which will be described in more detail below, the commercial formulations tested generally showed much lower antimicrobial effect than the inventive formulations. While not wishing to be bound to any specific theory, this observation is believed to be based on that the inventive combination of AHAs and high concentrations of humectants provide superior antimicrobial activity.

In preferred, non-limiting embodiments, the compositions of the invention further comprise up to 2% by weight of classified conventional preservatives, such as those of reference No. 1.

Keratolytic and Hygroscopic Agents

An AHA is an organic carboxylic acid in which there is a hydroxy group at the two (2), or alpha (α), position of the carbon chain. Important members of the group of AHAs are found in foods, and others have natural biological origins. Lactic acid, glycolic acid, tartaric acid, malic acid and citric acid are examples of substances belonging to the AHA group. Lactate is also a component of the natural hygroscopic material of the stratum corneum and constitutes about 12% of this material.[2] In guinea pig footpad corneum it has been shown that both lactic acid and sodium lactate increase the water holding capacity and skin extensibility.[3] When the pH increases, the adsorption of lactic acid decreases, due to the ionization of the acid.[3]

Salicylic acid is a beta-hydroxy acid and is often used in acne preparations to open-up clogged pores which facilitates the outflow of sebum and reduces risks for acne.

Urea is a naturally occurring humectant in human skin and it has also been discovered as a barrier-improving substance. The most well-known dermatologic effects from urea comes from its generally accepted property of unfolding proteins, thus solubilizing them and/or denaturing them.[4-6] Pieces of upper epidermis kept in saturated urea solutions change mechanically and lose their original quaternary structure.[4] Urea can also be used for avulsing dystrophic nails, and a preparation with 40% urea has been shown to be slightly more effective in removing the nail than a formulation with 22%, but was also more irritating. Urea is also used as a keratoplastic agent (at 40%) to increase the bioavailability of the drug in the treatment of onychomycosis.

Urea is conventionally being used as a 10% cream for the treatment of ichthyosis and hyperkeratotic skin disorders, and in lower concentrations for the treatment of dry skin. Urea is decomposed to ammonia and is therefore often combined with lactic acid to control pH of the formulations, as e.g. disclosed in GB 1,232,569 A. In the treatment of onychomycosis, urea has been added to a medicinal formulation at 40% as a keratoplastic agent to increase the bioavailability of the drug.[7]

High concentrations (about 10%) of urea in creams are used in the therapy of ichthyosis and other hyperkeratotic conditions. In seven patients with severe ichthyosis a pronounced keratolytic effect was noticed and the skin became soft and pliable.[8] Recent studies also show that certain urea-formulations can improve skin barrier function and prevent eczema.[9-10]

Panthenol is a precursor to vitamin B5 and is also found to be a humectant. Topically applied panthenol is reported to penetrate the skin and hairs and to be trans-formed into pantothenic acid[11-12]. Panthenol is found in topical treatments for rhinitis, conjunctivitis, sunburn, and for wound healing (ulcers, burns, bed sores, and excoriations); usually 2% is used.[11, 13] Treatment of sodium lauryl-sulphate (SLS)-induced irritated skin with panthenol accelerates skin barrier repair and stratum corneum hydration[14]. Moreover, skin redness (inflammation) decreased more rapidly by panthenol treatment.[14]

Clinical Studies on Hyperkeratotic Conditions on Related Formulations with Urea and AHA A number of clinical studies are available where the efficacy of humectants and keratolytic agents are monitored on dry skin. For example, in two controlled double-blind studies the efficacy of two ammonium lactate emulsions (corresponding to 12% and 5% lactic acid) was compared with that of a petrolatum-based therapeutic cream's and with that of a control lotion.[16] The products were randomized to left or right sides on 129 subjects with xerosis. The severity of the xerosis was evaluated clinically as degree of scaling, roughness, erythema and fissures. After about a week, the areas treated with the lactate emulsions were statistically significantly superior to those treated with the control products.[16] The mean severity score was also significantly reduced throughout the regression period (2-4 weeks).

In another double-blind study on 41 patients with xerosis on the lateral aspect of both legs, 12% ammonium lactate lotion was compared with a lotion containing 5% lactic acid and 2.5% sodium pyrrolidone carboxylic acid.[17] The study showed that 12% ammonium lactate was more effective in reducing the severity of dry skin than the reference lotion. Seven minor complaints were reported by the patients.

No difference in effect, however, was found between a cream with 7.5% lactic acid and 12% lactic acid lotion in a double-blind study on 11 psoriatic patients with xerosis.[18] Clinical grading was performed on days 0, 14 and 21 during the 3-week course of treatment, and at day 35 (two weeks post-treatment). Both preparations caused a slight burning/stinging sensation, but not on non-lesional sites. A 5% lactic acid preparation proved just as effective as the 12% lactate lotion during treatment, but the effect of the latter lasted significantly longer.[19]

Non-invasive methods have been used to assess the effects of AHA on dry skin.[20-21] Twice daily treatment with 12% ammonium lactate lotion for a month reduced the severity scores for dryness of the skin on the legs in 24 women.[20-21] Furthermore, the hydration values increased (measured with a corneometer) and improvement in some other parameters was also noted. Image analysis of squames removed by adhesive tape could also be used successfully to distinguish between formulations with and without AHA.[20-21]

Treatment of xerosis on the plantar surface of the feet for two weeks gave more pronounced improvement in skin roughness, fissures and dryness by a 40% urea cream than from a 12% ammonium lactate lotion.[22] No influence on skin barrier function was noted from urea-treatment. Both therapies showed sustained benefit during the next two weeks.

By inclusion of the appropriate amounts of the above actives (i.e. AHA, urea, panthenol and glycerin), the inventive composition is believed to exhibit the beneficial properties in the clinical studies as set out above.

None of the above studies addressed the antimicrobial effects of the formulations and the normalization of skin with potential influence of skin blood flow

AHA

The present inventors have found lactic acid, and glycolic acid, both when used alone, and in combination, to produce particularly antimicrobial formulations. The inventive formulation therefore comprises lactic acid, glycolic acid, or a combination thereof. According to the invention, other AHAs may additionally be included in the inventive formulation. Such other AHAs are preferably selected from tartaric acid, malic acid, methyl lactic acid, 1-hydroxybutanoic acid, 2-hydroxypentanoic acid, hydroxycaprylic acid, and citric acid. Salts thereof, such as alkali metal salts, especially of sodium and potassium, ammonium salts, and tri-ethanol amine salts, may also be used in order to partially neutralize the pH.

The inventive formulation preferably comprises at least 10% by weight of lactic acid and/or glycolic acid, more preferably at least 13% by weight, more preferably an amount of at least 14.5% by weight, and especially preferred is an amount of at least 15% by weight.

The one or more AHAs are contained in an amount of up to preferably 40% by weight calculated as acid, more preferably up to about 30%, and most preferably up to about 22.5%.

AHAs most commonly used in topical applications are typically glycolic acid, lactic acid, malic acid and citric acid. Glycolic acid has the smallest molecular size and therefore the greatest bioavailability, followed by lactic acid. Tartaric acid, on the other hand, is a larger molecule, which has lower bioavailability and also may be difficult to dissolve in the vehicle. Consequently, when used in the composition, e.g. tartaric acid will generally be included in lower amounts.

The AHAs will be selected so that the AHAs are dissolved in the particular composition. Salts of the AHAs could also be used, such as e.g. the sodium and potassium salts. A salt of a particular AHA can be used interchangeably with the AHA in its acid form, as long as the salt will be soluble in the resulting composition, and a dermatologically acceptable pH value can be obtained.

Urea

According to the invention, urea is contained in an amount of up to preferably 40% by weight, more preferably up to about 25%, and most preferably up to about 22.5%.

Panthenol

According to the invention, panthenol is contained in an amount of up to 20% by weight, more preferably up to about 10%, and most preferably up to about 7.5%.

Glycerol

According to the invention, glycerol is contained in an amount of up to 20% by weight, and more preferably up to about 10%, and most preferably up to about 7.5%.

The total amount of the above four active agents may range from 40 up to preferably 80% by weight of the composition, and more preferably from 40 to 60% by weight.

Accordingly, in the inventive topical composition, the amount of said one or more alpha-hydroxy acids may be up to 40% by weight; the amount of urea up to 40% by weight; the amount of glycerol up to 20% by weight; and, the amount of panthenol may be up to 20% by weight, wherein the total amount of the above components amounts to up to 80% by weight of the composition.

Dry hyperkeratotic skin, such as in eczema of the hands, atopic eczema, ichthyosis and psoriasis are also targeted diseases. In addition, patients with acne, and other diseases where overgrowth of microorganisms are believed to be involved in the disease pattern (e.g. skin mucosis), will benefit from the treatment with the inventive composition, especially in instances where the overgrowth of microorganisms is associated with presence of hyperkeratotic skin. Another type of skin defects which will benefit from the treatment includes signs of ageing skin, such as hyperpigmentation and rough skin.

Formulations according to the invention designed to treat body areas sensitive to stinging (e.g. the facial area in the case of acne) will contain the active ingredients in the amounts as specified above, but when included in a total amount of more than 40% by weight, the actives should be balanced as far as possible, so that less AHA and urea will be included in favour of using higher amounts of the low-stingers glycerin and panthenol. Higher AHA concentrations will be used when signs of skin ageing are being targeted and the duration of the treatment is shorter compared to treatment of acne.

pH

The pH value of the composition can be adjusted using more or less AHA salts, and also by the inclusion of a suitable base, such as e.g. NaOH, and ammonia.

Vehicles

A generally preferred vehicle takes the form of an emulsion. This especially applies for the treatment of feet. In the case of an emulsion, the essential elements that constitute the delivery system for the active ingredients are water and an oil phase to form the basic emulsion, with vegetable oils, mineral oil and other conventional oleaginous cosmetic bases being suitable for the oil phase. The composition in the case of an emulsion also employs emulsifying surfactants, such as PEG-20 methyl glucose sesquie stearate, glyceryl stearate, PEG-100 stearate, ceteareth-21, ceteareth-2 and, optionally, conventional emulsifying stabilizers such as methyl glucose sesquie stearate, sorbitan stearate, ceteraryl alcohol, and behenyl alcohol.

As additional elements, conventional cosmetic additives may be added to the composition. Principle additives include fragrances, anti-oxidants, preservatives, pigments or colorants. These are generally present in amounts necessary to provide the desired effect, generally between 0.01 and 5%, by weight of the composition.

Other possible delivery forms are aqueous gels and more rigid sticks of the active ingredients. Thickening agents commonly used in topical formulations include viscous liquids such as polyethylene glycol, synthetic polymers such as carbomer, vegetable gums (e.g. xanthan gum) and derivates of cellulose (e.g. hydroxypropyl methyl cellulose). The concentration and combination of the thickeners determine the viscosity of the formulation, where appropriate combinations also can make the delivery form stiff, i.e. a stick product. Sticks may be more convenient to use on small body areas, such as the heels and other localized hyperkeratotic/pigmented areas. In the present invention thickeners which can be used at low pH are preferred (i.e. not carbomers). Transparent and fat-free gels are preferred when facial skin in acne patients are treated. The different formulations can also be used to impregnate wipes, which then can be used to facilitate treatment of the body surface.

The invention will now be further disclosed by means of the following Examples.

EXAMPLES

For the purpose of the below testing of the inventive composition a simple vehicle D4 having the composition as set out in Table 1 was prepared.

TABLE 1

Compositions, in percent by weight of the total formulation, of the vehicle D4, and of the two inventive compositions C3 (Example 1) and H81 (Example 2), respectively.

| Ingredients | C3 Conc | D4 Conc | H81 Conc |
|---|---|---|---|
| Aqua | 42.25 | 83.9 | 21.4 |
| Urea | 15 | 0 | 22.5 |
| Sodium Lactate | 7.2 | 0 | 10.8 |
| Lactic Acid | 5.6 | 0 | 8.4 |
| Tartaric Acid | 0.5 | 0 | 0.75 |
| Glycolic Acid | 3.15 | 0 | 4.75 |
| Panthenol | 5 | 0 | 7.5 |
| Glycerin | 5 | 0 | 7.5 |
| PEG-20 Methyl Glucose Sesquistearate | 3 | 3 | 3 |
| Methyl Glucose Sesquistearate | 3 | 3 | 3 |
| *Butyrospermum Parkii* Butter | 2.5 | 2.5 | 2.5 |
| Octyldodecanol | 2 | 2 | 2 |
| Behenyl Alcohol | 2 | 2 | 2 |
| *Simmondsia Chinensis* Seed Oil | 1.5 | 1.5 | 1.5 |
| Caprylyl Glycol | 1 | 1 | 1 |
| Menthol | 0.5 | 0.5 | 0.5 |
| Polyacrylate-1 Crosspolymer | 0.4 | 0.4 | 0.4 |
| Sodium Gluconate | 0.2 | 0.2 | 0.2 |
| Sodium Hydroxide | 0.2 | 0 | 0.3 |

Example 1

C3

A formulation according to the invention designated C3 having the composition as set out in Table 1 was formulated using vehicle D4, in the absence of any conventional preservatives or antimicrobial agents.

Example 2

H81

An inventive formulation using higher amounts of the inventive combination was also prepared, in which formulation the amounts of the active ingredients of the invention had been increased by 50%, as compared to the composition of Example 1. The overall content of the active ingredients of the invention was thus 60% by weight. The formulation was designated H81 and the composition thereof is set out in Table 1.

Example 3

The antimicrobial capacity of the inventive compositions C3 and H81, respectively, was compared to that of four different commercially available products specified in Table 2 below.

TABLE 2

Tested commercially available compositions designed for hyperkeratotic treatment, especially for feet.

Compeed Nattkräm för hälar, McNeil Sweden (3 aliquots of lot3400V + 1 aliquot of lot 0820VA): Aqua, urea, lactic acid, ethyhexyl palmitate, isopropyl palmitate, stearyl alcohol, glyceryl stearate, sorbitol, ceterareth-25, ceteareth-6, palmitic acid, stearic acid, parfum
Scholl Kräm för spruckna hälar. Active repair, SSL International plc, UK (Lot 1000260 exp 2013 November and lot P714021): Aqua, urea (25%), dimethicone, decyl oleate, petrolatum, lanolin, dicoyl pentaerytrityl distearyl citrate, cera microcristallina, glyceryl oleate, paraffin, keratin, hydrolyzed keratin, panthenol, aluminium stearate, propylene glycol, phenoxyethanol, carbomer, chlorphenesin, bisabolol, tocopheryl acetate, sorbitol, methylparaben, butylparaben, ethylparaben, propylparaben, isobutylparaben, BHA, citric acid, sodium phosphate, faex, potassium sorbate.
Raxal, Cheiron Pharma, Greece (Lot 021110, exp November 2013): Urea 40%, Aqua, Lactic acid, PPG-3 benzyl ether myristate, Diisopropyl adipate, Glyceryl stearate, PPG-15 stearyl ether, PEG-100 stearate, Dimethicone, Salicylic acid 2%, PPG-25-

TABLE 2-continued

Tested commercially available compositions designed for hyperkeratotic treatment, especially for feet.

laureth-25, Ceteraryl alcohol, Ammonium hydroxide, Bisabolol, Hectorite, Hydroxyethylcellulose, Sodium hydroxide, Phenoxyethanol, Benzoic acid, Dehydroacetic acid, Sorbitan sesquioleate, Benzyl alchol, Disodium EDTA, Sorbitan stearate.
LacUrex, Cheiron Pharma, Greece (Lot 0040710, exp July 2013): Aqua, Ammonium lactate 12%, Urea 10%, Paraffinum Liquidum, Panthenol, Niacinamide, Glycerin, Glyceryl stearate, Cetearyl alcohol, Dimethicone, Petrolatum, PEG-100 stearate, Cera alba, Ehylhexylglycerin, Caprylyl glycol, Sorbitan stearate, Hectorite, Hydroxymethyl-cellulose, Allantoin, Bisabolol, Sorbitan sesquioleate, Disodium EDTA, Phenoxyethanol.

For comparison purposes the vehicle D4 used in the inventive formulations A1, C3 and H81 was also tested for antimicrobial activity.

Test inoculums were prepared and added to the samples to achieve the following CFU ("colony forming units" or cells) per ml as follows:

Bacteria (*Staphylococcus aureus*): $10^5$-$10^6$ CFU/ml
Yeast: (*Candida albicans*): $10^5$-$10^6$ CFU/ml
Fungi: (*Aspergillus brasiliensis*): $10^5$-$10^6$ CFU/ml The samples were then placed into incubators for a total of 24 hr. At various time intervals after addition of the respective inoculums, viz. 1, 3, 6 and 24 hours, the amount of CFU microorganisms was determined by plated in agar. The plates were incubated at appropriate conditions and the number of counts was read. Initial readings at the time 0 are very sensitive to the exact point of time of measurement after addition of the inoculum, and consequently very hard to reproduce consistently. The initial readings have therefore been left out from the results as presented in Table 3 below.

As can be seen from the results as presented in Table 3 below, as expected, the vehicle itself (D4) had virtually no antimicrobial effect.

TABLE 3

| Product | Bacteria/Yeast/Fungi | Initial | 1 h | 3 h | 6 h | 24 h |
|---|---|---|---|---|---|---|
| 1 Compeed (Comparative) | *St. aureus* | $5.4 \times 10^5$ | 123 | 0 | 0 | 0 |
| | *Candida a.* | $8.0 \times 10^5$ | 4,500 | 0 | 0 | 0 |
| | *A brasiliensis* | $5.4 \times 10^5$ | 200,000 | 80,000 | 70,000 | 5,900 |
| 2 Scholl (Comparative) | *St. aureus* | $5.4 \times 10^5$ | 10 | 0 | 0 | 0 |
| | *Candida a.* | $8.0 \times 10^5$ | 0 | 0 | 0 | 0 |
| | *A brasiliensis* | $5.4 \times 10^5$ | 1,800 | 100 | 1 | 0 |
| 3 Raxal (Comparative) | *St. aureus* | $5.4 \times 10^5$ | 0 | 0 | 0 | 0 |
| | *Candida a.* | $8.0 \times 10^5$ | 0 | 0 | 0 | 0 |
| | *A brasiliensis* | $5.4 \times 10^5$ | 90 | 0 | 0 | 0 |
| 4 Lacurex (Comparative) | *St. aureus* | $5,4 \times 10^5$ | 100 | 0 | 0 | 0 |
| | *Candida a.* | $8.0 \times 10^5$ | 0 | 0 | 0 | 0 |
| | *A brasiliensis* | $5.4 \times 10^5$ | 220 | 10 | 0 | 0 |
| 5 C3 (Example 1 of the invention) | *St. aureus* | $5.4 \times 10^5$ | 0 | 0 | 0 | 0 |
| | *Candida a.* | $8.0 \times 10^5$ | 0 | 0 | 0 | 0 |
| | *A brasiliensis* | $5.4 \times 10^5$ | 0 | 0 | 0 | 0 |
| 6 H81 (Example 2 of the invention) | *St. aureus* | $6.7 \times 10^5$ | 0 | 0 | 0 | 0 |
| | *Candida a.* | $7.3 \times 10^5$ | 0 | 0 | 0 | 0 |
| | *A brasiliensis* | $3.7 \times 10^5$ | 0 | 0 | 0 | 0 |
| 7 D4 (Comparative-vehicle only) | *St. aureus* | $6.7 \times 10^5$ | 610,000 | 350,000 | 126,000 | 0 |
| | *Candida a.* | $7.3 \times 10^5$ | 1,200,000 | 1,100,000 | 930,000 | 610,000 |
| | *A brasiliensis* | $3.7 \times 10^5$ | 230,000 | 200,000 | 200,000 | 150,000 |

Of the commercial products tested, LacUrex and Raxal were the most potent ones. Raxal, however, does not exhibit the inventive combination of actives, and is therefore not expected to have the beneficial effects as set out above which can be derived from the actives. The antimicrobial effect observed in the case of Raxal is likely to be due to conventional preservatives included in the composition.

The inventive composition C3 of Example 1 exhibited a very rapid killing rate. The composition of Example 2, i.e. H81, exhibited an even higher killing rate. As can be seen, only the two inventive compositions accomplished a total killing of the microorganisms tested within merely 1 hour.

Example 4

In this Example LacUrex was tested against the inventive composition of Example 1, i.e. C3. The two compositions tested were applied onto the entire feet of three different persons in a bilateral and randomised manner.

After different time intervals the area between the toes were sampled for amount of microorganisms. The sample area of the skin was about 1 $cm^2$ for each sample taken. The samples were taken with sterile cotton swabs, which were then placed in sterile liquid for testing in laboratory for aerobic bacteria (no fungi and no mould were detected in the samples).

An initial sample was taken from the skin area between the big toe and the index toe of each foot of each person at the time 0, i.e. just before application of the two different formulations. The formulations were then applied and the feet were allowed to dry in the air for 30 minutes, i.e. without socks on the feet.

After 30 minutes, samples were taken from the skin area between the index toe and the middle toe of each foot of each person. Thereafter, the subjects put on clean socks on their feet, and shoes. After 2 hours samples were taken from the next skin area between the middle toe and the forth toe of each foot of persons Nos. 2 and 3, after 3 hours samples were taken from the skin area between the forth toe and the little toe of persons Nos. 2 and 3, and finally, after 4.5 hours, samples were taken from the skin area between the fourth toe and the little toe of each foot of person No. 1.

The results are summarized in the Table 4 below.

TABLE 4

| Time | Person No. | C3 (CFU/sample) | LacUrex (CFU/sample) |
|---|---|---|---|
| 0 | 1 | 3,000 | 1,600 |
|   | 2 | 2,800 | 2,800 |
|   | 3 | 2,800 | 1,400 |
| 30 minutes | 1 | <2 | <2 |
|   | 2 | <2 | <2 |
|   | 3 | 4 | 1,800 |
| 2 hours | 2 | 400 | 2,400 |
|   | 3 | 6 | 2,000 |
| 3 hours | 2 | 8 | 1,600 |
|   | 3 | 90 | 3,000 |
| 4.5 hours | 1 | 4 | 3,000 |

As can be seen from the above Table 4, recolonization of bacteria on the feet in the case of the inventive formulation was markedly reduced, and was kept at a level next to zero throughout the whole testing period (4.5 hours), while the bacteria count returned to the initial value already at a time about 2 hours (or possibly earlier) after application of LacUrex.

Accordingly, the inventive formulation exhibits a long-term antimicrobial effect. This effect is believed to be due to the inventive combination of actives, which may be less volatile than the preservatives and microbial agents used in conventional formulations, and which will therefore produce a more sustained effect.

This long-term antimicrobial effect will make the inventive formulation suitable for healing open sores, and will make the required frequency of application of the formulation in order to achieve a given antimicrobial effect substantially reduced, thereby making the formulation more apt for use by persons with a sensitive skin, or otherwise sensitive to treatment of the skin by topical application of a formulation thereto.

The present invention is not limited to the above-described preferred embodiments. Various alternatives, modifications and equivalents may be used. Therefore, the above embodiments should not be taken as limiting the scope of the invention, which is defined by the appending claims.

REFERENCES

1. Buzek J, Ask B. REGULATION (EC) No 1223/2009° F. THE EUROPEAN PARLIAMENT AND OF THE COUNCIL of 30 Nov. 2009 on cosmetic products. Official Journal of the European Union 2009:L342/59-L42/209.
2. Jacobi O K. Moisture regulation in the skin. Drug Cosmet. Ind. 1959; 84:732-812.
3. Middleton J. Development of a skin cream designed to reduce dry and flaky skin. J Soc Cosmet Chem 1974; 25:519-34.
4. Hellgren L, Larsson K. On the effect of urea on human epidermis. Dermatologica 1974; 149:89-93.
5. Ashton H, Frenk E, Stevenson C J. Therapeutics XIII. Urea as a topical agent. Br. J. Dermatol. 1971; 84:194-96.
6. Kunz D, Brassfield T S. Hydration of macromolecules. II. Effects of urea on protein hydration. Arch Biochem. Biophys. 1971; 142:660-64.
7. Fritsch H, Stettendorf S, Hegemann L. Ultrastructural changes in onychomycosis during the treatment with bifonazole/urea ointment. Dermatology 1992; 185(1):32-6.
8. Swanbeck G. A new treatment of ichthyosis and other hyperkeratotic conditions. Acta Derm-Venereol. (Stockh), 1968; 48:123-27.
9. Lodén M. Clinical evidence for the use of urea. In: Lodén M, Maibach H I, editors. Dry Skin and Moisturizers: Chemistry and function. Boca Raton: CRC Press Taylor & Francis Group 2006. p. 211-25.
10. Lodén M. Prevention or promotion of dryness and eczema by moisturizers? Expert Rev. Dermatol 2008; 3(6):667-76.
11. Schmid-Grendelmeier P, Wyss M, Elsner P. Contact allergy to dexpanthenol. A report of seven cases and review of the literature. Dermatosen 1995; 43:175-78.
12. Final Report on the safety assessment of panthenol and pantothenic acid. J Am Coll Toxicol 1987; 6:139-63.
13. Martindale: The Complete Drug Reference. London: Pharmaceutical Press; 2005.
14. Proksch E, Nissen H P. Dexpanthenol enhances skin barrier repair and reduces inflammation after sodium lauryl sulphate-induced irritation. J Dermatol Treatm 2002; 13:173-78.
15. Wehr R, Krochmal L, Bagatell F, W. R. A controlled two-center study of lactate 12% lotion and a petrolatum-based creme in patients with xerosis. Cutis 1986; 37:205-09.
16. Wehr R F, Kantor I, Jones E L, McPhee M E. A controlled comparative efficacy study of 5% ammonium lactate lotion versus an emollient control lotion in the treatment of moderate xerosis. J Am Acad Dermatol 1991; 25:849-51.
17. Rogers R S, Callen J, Wehr R, Krochmal L. Comparative efficacy of 12% ammonium lactate lotion and 5% lactic acid lotion in the treatment of moderate to severe xerosis. J Am Acad Dermatol 1989; 21:714-16.
18. Green L, Cole G W. A comparison study of 7.5% lactic acid cream and 12% lactic acid lotion in psoriatic patients with xerosis cutis. Cos Derm 1994; 7:44-45.
19. Dahl M V, Dahl A C. 12% lactate lotion for the treatment of xerosis. Arch Dermatol 1983; 119:27-30.
20. Vilaplana J, Coll J, Trullás C, Axón A, Pelejero C. Clinical and non-invasive evaluation of 12% ammonium lactate emulsion for the treatment of dry skin in atopic and non-atopic subjects. Acta Derm Venereol (Stockh) 1992; 72:28-33.
21. Prall J K, Theiler R F, Bowser P A, Walsh M. The effectiveness of cosmetic products in alleviating a range of skin dryness conditions as determined by clinical and instrumental techniques. Int J Cosmet Sci 1988; 8:159-74.
22. Ademola J, Frazier C, Kim S J, Theaux C, Xaudez X. Clinical evaluation of 40% urea and 12% ammonium lactate in the treatment of xerosis. Am J Clin Dermatol 2002; 3:217-22.

The invention claimed is:

1. A topical composition comprising:
   15 to 22.6% by weight, calculated as free acid, of one or more alpha-hydroxy acids comprising lactic acid and/or glycolic acid,
   wherein the lactic acid and/or glycolic acid is contained in a total amount of 14.5% to 21.9% by weight of the composition;
   15 to 22.5% by weight of urea;
   5 to 7.5% by weight of glycerol; and
   5 to 7.5% by weight of panthenol,
   in a dermatologically acceptable vehicle,
   wherein the total amount of said alpha-hydroxy acid(s), urea, glycerol, and panthenol constitutes from 40% up to 60.1% by weight of the composition.

2. The topical composition of claim 1, further comprising salicylic acid.

3. The topical composition of claim 1, further comprising a conventional preservative and a fatty alcohol.

4. The topical composition of claim 1, wherein retinol, or a derivative thereof is present.

5. The topical composition of claim 1, further comprising behenyl alcohol.

6. The topical composition of claim 1, further comprising a blood flow stimulating agent.

7. The topical composition of claim 1, wherein the vehicle is an emulsion.

8. A method of treating a subject with hyperkeratotic skin, comprising administrating topically to the affected skin a composition of claim 1.

9. The topical composition of claim 1, wherein the lactic acid and/or glycolic acid is contained in an amount of at least 15% by weight.

10. The method of claim 8, wherein the hyperkeratotic skin is associated with a medical condition.

11. The method of claim 10, wherein the medical condition is diabetes.

12. The method of claim 10, wherein the medical condition is selected from the group consisting of eczema of the hands, atopic eczema, ichthyosis, and psoriasis.

13. The method of claim 8, wherein hyperkeratotic skin is on a foot.

14. The method of claim 8, wherein the hyperkeratotic skin is associated with acne or skin mucosis.

* * * * *